United States Patent [19]

Jeanmart et al.

[11] 4,124,711
[45] Nov. 7, 1978

[54] DERIVATIVES OF DITHIEPINO[1,4][2,3-C]PYRROLE

[75] Inventors: Claude Jeanmart, Brunoy; Andre Leger, Paris, both of France

[73] Assignee: Rhone-Poulenc Industries, Paris, France

[21] Appl. No.: 769,737

[22] Filed: Feb. 17, 1977

[30] Foreign Application Priority Data

Feb. 20, 1976 [FR] France ............................ 76 04713
Nov. 22, 1976 [FR] France ............................ 76 35096

[51] Int. Cl.² .................. A61K 31/55; C07D 513/04
[52] U.S. Cl. ................................ 424/250; 544/362; 544/363; 544/364; 544/373
[58] Field of Search ............... 260/268 BC, 268 BQ; 424/250

[56] References Cited

U.S. PATENT DOCUMENTS 3,948,917  4/1976  Jeanmart et al. ............ 260/268 BQ
4,021,554  5/1977  Cotrel et al. ................... 424/250

Primary Examiner—Paul M. Coughlan, Jr.
Attorney, Agent, or Firm—Stevens, Davis, Miller & Mosher

[57] ABSTRACT

Compounds of the formula:

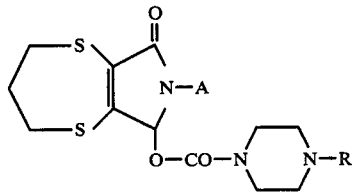

wherein A represents a phenyl, pyrid-2-yl, quinol-2-yl or 1,8-naphthyridin-2-yl radical, each such radical being optionally substituted by a halogen atom, an alkyl radical of 1 through 4 carbon atoms, an alkoxy radical of 1 through 4 carbon atoms, the cyano or nitro radical, and R represents hydrogen or an alkyl radical of 1 through 4 carbon atoms, an alkenyl radical of 2 through 4 carbon atoms or an alkanoyl radical of 1 through 4 carbon atoms, possess pharmacological properties and are particularly active as tranquillizers, anti-convulsant agents, decontracturants and agents to produce hypnosis.

15 Claims, No Drawings

DERIVATIVES OF DITHIEPINO[1,4][2,3-C]PYRROLE

This invention relates to new therapeutically useful dithiepino[1,4][2,3-c]pyrrole derivatives, processes for their preparation and pharmaceutical compositions containing them.

The new dithiepino[1,4][2,3-c]pyrrole derivatives of the present invention are those compounds of the general formula:

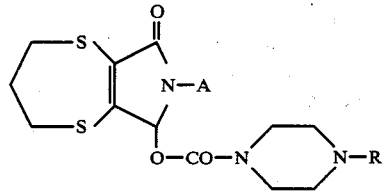
I wherein A represents a phenyl, pyrid-2-yl, quinol-2-yl or 1,8-naphthyridin-2-yl radical, each such radical being optionally substituted by a halogen atom (preferably chlorine), an alkyl radical containing 1 to 4 carbon atoms (preferably methyl), an alkoxy radical containing 1 to 4 carbon atoms (preferably methoxy), a cyano radical or a nitro radical, and R represents a hydrogen atom or an alkyl radical containing 1 to 4 carbon atoms (preferably methyl), an alkenyl radical containing 2 to 4 carbon atoms (preferably allyl) or an alkanoyl radical containing 1 to 4 carbon atoms (e.g. propionyl or butyryl), and — when appropriate — acid addition salts thereof.

According to a feature of the invention, the new compounds of general formula I are prepared by the process which comprises reacting a 1-chlorocarbonyl-piperazine of the general formula:

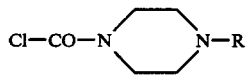
II (wherein R is as hereinbefore defined) with a dithiepino[1,4][2,3-c]pyrrole derivative of the general formula:

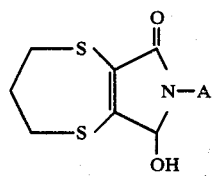
III wherein A is as hereinbefore defined.

The reaction can be carried out by reacting a compound of general formula II with a compound of general formula III in the form of an alkali metal salt, optionally prepared in situ, in an anhydrous organic solvent, such as dimethylformamide or tetrahydrofuran, at a temperature below 60° C.

It is also possible to react a compound of general formula II, optionally in the form of an acid addition salt (preferably the hydrochloride), with a compound of general formula III, the reaction being carried out in pyridine and, when an acid addition salt of the reactant of formula II is used, optionally in the presence of a tertiary amine such as triethylamine which liberates the compound of general formula II from its salt.

The dithiepino[1,4][2,3-c]pyrrole derivatives of general formula III can be obtained by partial reduction of an imide of the general formula:

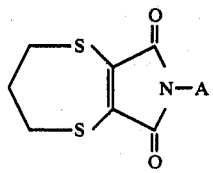
IV wherein A is as hereinbefore defined. The reduction is generally effected by means of an alkali metal borohydride, in an organic or aqueous-organic solution, for example in a dioxan-tetrahydrofuran or dioxan-methanol or dioxan-water or methanol-water or ethanol-water mixture.

The imides of the general formula IV can be obtained by reacting an amine of the general formula:

$H_2N - A$      V (wherein A is as hereinbefore defined) with the anhydride of 6,7-dihydro-5H-1,4-dithiepin-2,3-dicarboxylic acid. The reaction is generally carried out by heating the reactants in an organic solvent such as acetic acid, dimethylformamide, acetonitrile or diphenyl ether, or a mixture of such solvents, in the presence or absence of a carbodiimide such as dicyclohexylcarbodiimide or 3-(3-diethylaminopropyl)-1-isopropylcarbodiimide.

The anhydride of 6,7-dihydro-5H-1,4-dithiepin-2,3-dicarboxylic acid can be prepared by the hydrolysis in an acid medium of 6,7-dihydro-5H-1,4-dithiepin-2,3-dicarbonitrile. Generally the reaction is preferably carried out in about 20N sulphuric acid at a temperature between 100° and 125° C.

6,7-Dihydro-5H-1,4-dithiepin-2,3-dicarbonitrile can be obtained by the action of 1,3-dibromopropane on the disodium salt of 2,3-dimercaptomaleonitrile. The reaction is generally carried out in an inert organic solvent such as 1,2-dimethoxyethane or dimethylformamide at a temperature between 20° C. and the boiling point of the reaction mixture.

The disodium salt of 2,3-dimercaptomaleonitrile can be prepared in accordance with the process described by H. R. Schweizer, Helv. Chim. Acta., 52, 2228 (1969).

The piperazine derivatives of general formula II, wherein R represents an alkanoyl radical, can be obtained by the action of phosgene in toluene solution at a temperature of about −5° C. on a piperazine derivative of the general formula:

VI wherein $R_1$ represents the corresponding alkanoyl radical containing 1 to 4 carbon atoms.

The piperazine derivatives of general formula VI can be obtained from piperazine by applying methods known per se for the preparation of amides, such as the action of an acid of the general formula:

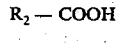
$R_2 - COOH$      VII (wherein $R_2$ represents a hydrogen atom or an alkyl radical containing 1 to 3 carbon atoms), or of a derivative of such an acid such as a halide, an ester, the anhydride, a mixed anhydride, the amide or the azide, on piperazine. The piperazine derivative of general formula VI can be separated from the disubstituted piperazine, which is formed simultaneously, by application of physical or chemical methods.

According to another feature of the invention, the compounds of general formula I are prepared by the process which comprises reacting a piperazine of the general formula:

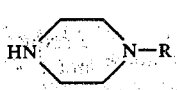
VIII (wherein R is as hereinbefore defined) with a mixed carbonate of the general formula:

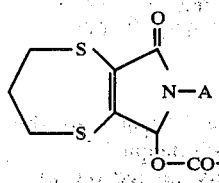
IX wherein A is as hereinbefore defined and Ar represents a phenyl radical which is optionally substituted by an alkyl radical containing 1 to 4 carbon atoms or by a nitro radical. The reaction is generally carried out in an anhydrous organic solvent such as acetonitrile at a temperature between 0° and 50° C.

The mixed carbonates of general formula IX can be obtained by reacting a chloroformate of the general formula:

$$Cl - CO - O - Ar \quad X$$

(wherein Ar is as hereinbefore defined) with a dithiepino[1,4][2,3-c]pyrrole derivative of general formula III. The reaction is generally carried out in a basic organic solvent such as pyridine or in an organic solvent such as tetrahydrofuran in the presence of an alkaline condensation agent.

According to a still further feature of the invention, the compounds of general formula I, wherein R represents an alkanoyl radical, are prepared by reacting an acid of general formula VII, or a reactive derivative of the acid such as a halide, preferably the chloride, the anhydride, a mixed anhydride, the amide or the azide, with a compound of general formula I wherein R represents a hydrogen atom, that is to say a compound of the general formula:

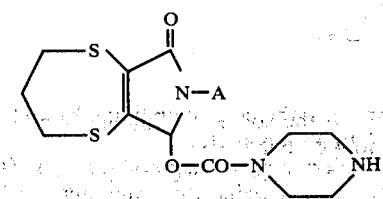
XI wherein A is as hereinbefore defined.

When an acid of the general formula VII is used, the reaction is generally carried out in an inert organic solvent, such as acetonitrile, methylene chloride, dimethylformamide or ethyl acetate, in the presence of a condensation agent such as dicyclohexylcarbodiimide or N,N-carbonyl-diimidazole at a temperature between 20° and 60° C.

When a halide of an acid of general formula VII (preferably the chloride) is used, the reaction is carried out in an organic solvent such as methylene chloride in the presence of an acid acceptor, for example pyridine or triethylamine, at a temperature between 0° and 30° C.

When the anhydride of an acid of general formula VII or a mixed anhydride is used, the reaction is generally carried out by heating the reactants at a temperature of between 30° and 100° C.

When the amide of an acid of general formula VII is used, the reaction is generally carried out by heating at a temperature above 100° C., optionally in an organic solvent such as an aromatic hydrocarbon and preferably in the presence of iodine.

When the azide of an acid of general formula VII is used, the reaction is generally carried out in an organic solvent such as dioxan in the presence of magnesium oxide at a temperature between 25° and 60° C.

The compounds of general formula XI can be obtained by the action of 1-chlorocarbonylpiperazine on a dithiepino[1,4][2,3-c]pyrrole derivative of general formula III or by the action of piperazine on a mixed carbonate of general formula IX.

The compounds of general formula XI can also be obtained, according to another feature of the invention, from a compound of the general formula:

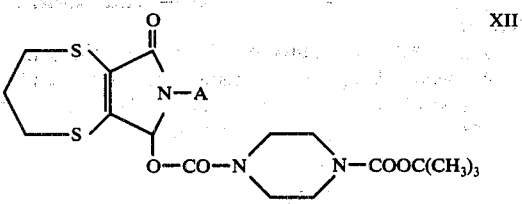
XII (wherein A is as hereinbefore defined) by treatment with trifluoroacetic acid, preferably at a temperature between 0° and −10° C.

The compounds of general formula XII can be obtained by the action of 4-chlorocarbonyl-1-t.-butoxycarbonylpiperazine on a dithiepino[1,4][2,3-c]pyrrole derivative of general formula III. The reaction is generally carried out in an organic solvent such as methylene chloride in the presence of an acid acceptor, for example pyridine or triethylamine, at a temperature between 0° and 30° C.

4-Chlorocarbonyl-1-t.-butoxycarbonylpiperazine can be obtained by the action of phosgene, in toluene solution, on 1-t.butoxycarbonylpiperazine at a temperature of about −5° C.

1-t.-butoxycarbonylpiperazine can be obtained by the action of piperazine hydrochloride on t.-butyl azidoformate.

The dithiepino[1,4][2,3-c]pyrrole derivatives of general formula I obtained by the aforementioned processes can be purified by physical methods such as crystallisation or chromatography, or by chemical methods such as the formation of salts, crystallisation of the salts and decomposition of them in an alkaline medium. In carrying out the said chemical methods the nature of the anion of the salt is immaterial, the only requirement being that the salt must be well-defined and readily crystallisable.

The compounds of general formula I, and more particularly those wherein R represents a hydrogen atom or an alkyl or alkenyl radical, may be converted by methods known per se into acid addition salts.

The acid addition salts may be obtained by the action of acids on the new compounds in appropriate solvents. As organic solvents there may be used alcohols, ketones, ethers or chlorinated hydrocarbons. The salt which is formed is precipitated, if necessary after concentration of the solution, and is isolated by filtration or decantation.

By the term "methods known per se" as used in this specification is meant methods heretofore used or described in the chemical literature.

The dithiepino[1,4][2,3-c]pyrrole derivatives of the invention and, where appropriate, their acid addition salts possess valuable pharmacological properties. They are particularly active as tranquillisers, anti-convulsant agents, decontracturants and agents to product hypnosis. In animals (mice) they have proved active as such at doses of between 1 and 100 mg/kg animal body weight administered orally, in particular in the following tests:

(i) electrical battle according to a technique similar to that of Tedeschi et al., J. Pharmacol., 125, 28 (1959), (ii) pentetrazole-induced convulsion according to a technique similar to that of Everett and Richards, J. Pharmacol., 81, 402 (1944), (iii) supramaximal electric shock according to the technique of Swinyard et al., J. Pharmacol., 106, 319 (1952), (iv) mortality on treatment with strychnine according to a technique similar to that of F. Barzaghi et al., Arzneimittel-Forschung, 23, 683 (1973), and (v) locomotor activity according to the technique of Courvoisier, Congres des Medecins Alienistes et Neurologistes, Tours, 8th-13th June 1959, and Julou, Bulletin de al Societe de Pharmacie de Lille, No. 2, January 1967, p. 7.

Furthermore, the compounds of the invention exhibit a low toxicity; their $LD_{50}$ when administered orally to mice is generally greater than 900 mg/kg animal body weight.

Preferred dithiepino[1,4][2,3-c]pyrrole derivatives of the invention are those of general formula I wherein A represents a pyrid-2-yl or 1,8-naphthyridin-2-yl radical optionally substituted by a halogen (preferably chlorine) atom or by an alkoxy radical containing 1 to 4 carbon atoms (preferably methoxy), and R represents an alkyl radical containing 1 to 4 carbon atoms (preferably methyl) or an alkenyl radical containing 2 to 4 carbon atoms (preferably allyl). Of especial interest are those dithiepino[1,4][2,3-c]pyrrole derivatives of general formula I obtained as products in Examples 2, 10, 11 and 15 which follow.

For therapeutic purposes, the dithiepino[1,4][2,3-c]pyrrole derivatives of general formula I may be employed as such or in the form of non-toxic acid addition salts, i.e. salts containing anions which are relatively innocuous to the animal organism in therapeutic doses of the salts (such as hydrochlorides, sulphates, nitrates, phosphates, acetates, propionates, succinates, benzoates, fumarates, maleates, tartrates, theophylline-acetates, salicylates, phenolphthalinates and methylene-bis-β-hydroxynaphthoates) so that the beneficial physiological properties inherent in the bases are not vitiated by side effects ascribable to the anions.

The following non-limitative Examples illustrate the invention.

EXAMPLE 1

Triethylamine (48 cc) followed by anhydrous pyridine (120 cc) are added, at 10° C., to a suspension of 6-hydroxy-7-(4-nitrophenyl)-8-oxo-3,4,7,8-tetrahydro-2H,6H-dithiepino[1,4][2,3-c]pyrrole (9.7 g) and 1-chlorocarbonyl-4-methylpiperazine hydrochloride (54.0 g) in anhydrous methylene chloride (300 cc). The reaction mixture is heated at 50° C. for 15 hours. After cooling, the mixture is diluted by adding methylene chloride (250 cc). The organic phase is washed with N sodium hydroxide solution (250 cc) and then six times with distilled water (total 1.5 liters), and is dried over anhydrous magnesium sulphate and evaporated to dryness. The residue is dissolved in boiling ethanol (100 cc) and a solution of fumaric acid (17.0 g) in boiling ethanol (250 cc) is added. After cooling for 15 hours at 2° C., the resulting crystals are filtered off, washed twice with iced ethanol (total 40 cc) and three times with diethyl ether (total 60 cc) and dried in air. The product obtained is treated with N sodium hydroxide solution (250 cc) and methylene chloride (100 cc); the aqueous phase is again extracted twice with methylene chloride (total 100 cc). The combined organic phases are washed three times with distilled water (total 300 cc), dried over anhydrous magnesium sulphate and evaporated to dryness. The residue is dissolved in boiling acetonitrile (30 cc) and diisopropyl ether (20 cc) is added to the solution. After cooling for 2 hours at 2° C., the crystals which have appeared are filtered off, washed twice with ethanol (total 20 cc) and three times with diisopropyl ether (total 30 cc) and dried under reduced pressure (0.2 mm Hg). 6-(4-Methylpiperazin-1-yl)carbonyloxy-7-(4-nitrophenyl)-8-oxo-3,4,7,8-tetrahydro-2H,6H-dithiepino[1,4][2,3-c]pyrrole (9.8 g), melting at 149° C., is thus obtained.

6-Hydroxy-7-(4-nitrophenyl)-8-oxo-3,4,7,8-tetrahydro-2H,6H-dithiepino[1,4][2,3-c]pyrrole used as starting material can be prepared in the following manner:

Preparation of the disodium salt of 2,3-dimercaptomaleonitrile according to H. R. Schweizer, Helv. Chim. Acta. 52, 2228 (1969).

Preparation of 6,7-dihydro-5H-1,4-dithiepin-2,3-dicarbonitrile (48.8 g), m.p. 106° C., by the action of 1,3-dibromopropane (121.2 g) on the disodium salt of 2,3-dimercaptomaleonitrile (112.0 g) in 1,2-dimethoxyethane at 55°-60° C. and subsequently under reflux.

Preparation of 6,7-dihydro-5H-1,4-dithiepin-2,3-dicarboxylic acid anhydride (35.1 g), m.p. 126° C., by hydrolysis of 6,7-dihydro-5H-1,4-dithiepin-2,3-dicarbonitrile (45.5 g) with sulphuric acid at 120°-125° C.

Preparation of 6,8-dioxo-7-(4-nitrophenyl)-3,4,7,8-tetrahydro-2H,6H-dithiepino[1,4][2,3-c]pyrrole (15.4 g), m.p. 232° C., by the action of 4-nitroaniline (8.3 g) and 3-(3-diethylaminopropyl)-1-isopropylcarbodiimide (11.9 g) on 6,7-dihydro-5H-1,4-dithiepin-2,3-dicarboxylic acid anhydride (12.1 g) in acetonitrile at the reflux temperature.

Preparation of 6-hydroxy-7-(4-nitrophenyl)-8-oxo-3,4,7,8-tetrahydro-2H,6H-dithiepino[1,4][2,3-c]pyrrole (12.1 g), m.p. 200° C., by the action of sodium borohydride (1.4 g) on 6,8-dioxo-7-(4-nitrophenyl)-3,4,7,8-tetrahydro-2H,6H-dithiepino[1,4][2,3-c]pyrrole (16.1 g) in a mixture of tetrahydrofuran and methanol (5:1 by volume) at between −20° C. and +2° C.

EXAMPLE 2

Triethylamine (46 cc) is added, at 10° C., to a suspension of 7-(5-chloropyrid-2-yl)-6-hydroxy-8-oxo-3,4,7,8-tetrahydro-2H,6H-dithiepino[1,4][2,3-c]pyrrole (12.6 g) and 1-chlorocarbonyl-4-methylpiperazine hydrochloride (48.0 g) in anhydrous methylene chloride (350 cc), and anhydrous pyridine (200 cc) is then added at 20° C. The reaction mixture is heated at 50° C. for 6 hours. After cooling, the mixture is diluted by adding methylene chloride (500 cc). The organic phase is washed six times with distilled water (total 3 liters), dried over anhydrous magnesium sulphate and evaporated. The residue is dissolved in boiling ethanol (200 cc). After cooling for 15 hours at 2° C., the resulting crystals are filtered off, washed three times with iced ethanol (total 75 cc) and three times with diethyl ether (total 75 cc) and dried under reduced pressure (20 mm Hg). The product obtained (12.5 g; m.p. 154° C.) is dissolved in a boiling mixture of ethanol (140 cc) and acetonitrile (40 cc). After filtering the boiling solution and then cooling it for 4 hours at 2° C., the crystals which have appeared are filtered off, washed twice with iced ethanol (total 20 cc) and then with diethyl ether (15 cc), and dried under reduced pressure (0.2 mm Hg). 7-(5-Chloropyrid-2-yl)-6-(4-methylpiperazin-1-yl)carbonyloxy-8-oxo-3,4,7,8-tetrahydro-2H,6H-dithiepino[1,4][2,3-c]pyrrole (8.6 g), melting at 156° C., is thus obtained.

7-(5-Chloropyrid-2-yl)-6-hydroxy-8-oxo-3,4,7,8-tetrahydro-2H,6H-dithiepino[1,4][2,3-c]pyrrole used as starting material can be prepared in the following manner:

Preparation of 7-(5-chloropyrid-2-yl)-6,8-dioxo-3,4,7,8-tetrahydro-2H,6H-dithiepino[1,4][2,3-c]pyrrole (27.4 g), m.p. 234° C., by the action of 2-amino-5-chloropyridine (12.8 g) on 6,7-dihydro-5H-1,4-dithiepin-2,3-dicarboxylic acid anhydride (20.2 g) in diphenyl ether at 160° C. in the presence of anhydrous acetic acid (0.5 cc).

Preparation of 7-(5-chloropyrid-2-yl)-6-hydroxy-8-oxo-3,4,7,8-tetrahydro-2H,6H-dithiepino[1,4][2,3-c]pyrrole (10.5 g), m.p. 168° C., by the action of sodium borohydride (2.1 g) on 7-(5-chloropyrid-2-yl)-6,8-dioxo-3,4,7,8-tetrahydro-2H,6H-dithiepino[1,4][2,3-c]pyrrole (17.2 g) in a mixture of methanol and tetrahydrofuran (1:5 by volume) at between −20° and +2° C.

EXAMPLE 3

Following the procedure of Example 2 but starting with 7-(5-chloropyrid-2-yl)-6-hydroxy-8-oxo-3,4,7,8-tetrahydro-2H,6H-dithiepino[1,4][2,3-c]pyrrole (7.9 g) and 1-chlorocarbonyl-4-ethylpiperazine hydrochloride (48.0 g) in a mixture of methylene chloride (250 cc) and anhydrous pyridine (100 cc) in the presence of triethylamine (40 cc), 7-(5-chloropyrid-2-yl)-6-(4L-ethylpiperazin-1-yl)carbonyloxy-8-oxo-3,4,7,8-tetrahydro-2H,6H-dithiepino[1,4][2,3-c]pyrrole (4.7 L g), melting at 130° C., is obtained after recrystallisation from acetonitrile (15 cc).

1-Chlorocarbonyl-4-ethylpiperazine hydrochloride can be prepared from 1-ethylpiperazine (74.6 g) and phosgene (129.0 g) in diethyl ether (500 cc) at 0° C. This gives 1-chlorocarbonyl-4-ethylpiperazine hydrochloride (115.7 g) which decomposes at about 270° C.

EXAMPLE 4

Following the procedure of Example 2 but starting with 7-(5-chloropyrid-2-yl)-6-hydroxy-8-oxo-3,4,7,8-tetrahydro-2H,6H-dithiepino[1,4][2,3-c]pyrrole (7.9 g) and 4-allyl-1-chlorocarbonylpiperazine hydrochloride (51.5 g) in a mixture of methylene chloride (250 cc) and anhydrous pyridine (100 cc) in the presence of triethylamine (40 cc), 6-(4-allylpiperazin-1-yl)carbonyloxy-7-(5-chloropyrid-2-yl)-8-oxo-3,4,7,8-tetrahydro-2H,6H-dithiepino[1,4][2,3-c]pyrrole (5.8 g), melting at 139° C., is obtained after recrystallisation from a mixture of acetonitrile (15 cc) and diisopropyl ether (50 cc).

4-Allyl-1-chlorocarbonylpiperazine hydrochloride can be prepared from 1-allylpiperazine (63.0 g) and phosgene (99.0 g) in diethyl ether (400 cc) at 0° C. This gives 4-allyl-1-chlorocarbonylpiperazine hydrochloride (86.1 g) which decomposes at about 200° C.

EXAMPLE 5

Triethylamine (56 cc) and anhydrous pyridine (140 cc) are added successively, at 10° C., to a suspension of 6-hydroxy-7-(5-methylpyrid-2-yl)-8-oxo-3,4,7,8-tetrahydro-2H,6H-dithiepino[1,4][2,3-c]pyrrole (10.3 g) and 1-chlorocarbonyl-4-methylpiperazine hydrochloride (63.0 g) in anhydrous methylene chloride (350 cc). The reaction mixture is heated at 50° C. for 15 hours. After cooling, the mixture is diluted by adding methylene chloride (250 cc). The organic phase is washed with 2N sodium hydroxide solution (250 cc) and then six times with distilled water (total 1.5 liters), dried over anhydrous magnesium sulphate and evaporated to dryness. The residue is dissolved in boiling ethanol (75 cc) and diisopropyl ether (75 cc) is added. After cooling for 15 hours at 2° C., the resulting crystals are filtered off, washed twice with iced ethanol (total 10 cc) and three times with diisopropyl ether (total 30 cc) and dried under reduced pressure (20 mm Hg). The product obtained (8.0 g; m.p. 144° C.) is dissolved in boiling ethanol (60 cc), and diisopropyl ether (30 cc) and decolourizing charcoal (0.5 g) are then added. After filtering the boiling solution and then cooling it for 4 hours at 2° C., the crystals which have appeared are filtered off, washed twice with iced ethanol (total 6 cc) and three times with diisopropyl ether (total 60 cc) and dried under reduced pressure (0.2 mm Hg). 6-(4-Methylpiperazin-1-yl)-carbonyloxy-7-(5-methylpyrid-2-yl)-8-oxo-3,4,7,8-tetrahydro-2H,6H-dithiepino[1,4][2,3-c]pyrrole (6.0 g), melting at 145° C., is thus obtained.

6-Hydroxy-7-(5-methylpyrid-2-yl)-8-oxo-3,4,7,8-tetrahydro-2H,6H-dithiepino[1,4][2,3-c]pyrrole used as starting material can be prepared in the following manner:

Preparation of 6,8-dioxo-7-(5-methylpyrid-2-yl)-3,4,7,8-tetrahydro-2H,6H-dithiepino[1,4][2,3-c]pyrrole (19.4 g), m.p. 270° C., by the action of 2-amino-5-methylpyridine (7.6 g) on 6,7-dihydro-1,4-dithiepin-2,3-dicarboxylic acid anhydride (14.1 g) in diphenyl ether at 200° C. in the presence of acetic acid (0.5 cc).

Preparation of 6-hydroxy-7-(5-methylpyrid-2-yl)-8-oxo-3,4,7,8-tetrahydro-2H,6H-dithiepino[1,4][2,3-c]pyrrole (12.5 g), m.p. 128° C., by the action of sodium borohydride (5.1 g) on 6,8-dioxo-7-(5-methylpyrid-2-yl)-3,4,7,8-tetrahydro-2H,6H-dithiepino[1,4][2,3-c]pyrrole (19.4 g) in a mixture of tetrahydrofuran and methanol (5:1 by volume) at between −20° C. and +2° C.

EXAMPLE 6

Triethylamine (69.5 cc) and anhydrous pyridine (174 cc) are added successively, at 10° C., to a suspension of 6-hydroxy-7-(5-nitropyrid-2-yl)-8-oxo-3,4,7,8-tetrahydro-2H,6H-dithiepino[1,4][2,3-c]pyrrole (14.1 g) and 1-chlorocarbonyl-4-methylpiperazine hydrochloride (78.0 g) in anhydrous methylene chloride (430 cc). The reaction mixture is heated at 45° C. for 15 hours. After cooling, the mixture is treated with distilled water (500 cc) and 10N sodium hydroxide solution (100 cc). The aqueous phase is extracted three times with methylene chloride (total 900 cc). The combined methylene chloride extracts are washed four times with distilled water (total 1 liter), dried over anhydrous magnesium sulphate and evaporated to dryness. The residue is treated with acetonitrile (150 cc). After cooling for two hours at 2° C., the insoluble crystals are filtered off, washed three times with iced acetonitrile (total 30 cc) and twice with diisopropyl ether (total 20 cc) and dried under reduced pressure (20 mm Hg). The product obtained (1.9 g; m.p. 180° C.) is dissolved in boiling acetonitrile (480 cc). After cooling for 2 hours at 2° C., the resulting crystals are filtered off, washed twice with iced acetonitrile (total 40 cc) and dried under reduced pressure (0.2 mm Hg). This gives 6-(4-methylpiperazin-1-yl)carbonyloxy-7-(5-nitropyrid-2-yl)-8-oxo-3,4,7,8-tetrahydro-2H,6H-dithiepino[1,4][2,3-c]pyrrole (10.4 g) melting at 182° C.

6-Hydroxy-7-(5-nitropyrid-2-yl)-8-oxo-3,4,7,8-tetrahydro-2H,6H-dithiepino[1,4][2,3-c]pyrrole used as starting material can be prepared in the following manner:

Preparation of 6,8-dioxo-7-(5-nitropyrid-2-yl)-3,4,7,8-tetrahydro-2H,6H-dithiepino[1,4][2,3-c]pyrrole (18.9 g), m.p. 230° C., by the action of 2-amino-5-nitropyridine (10.5 g) on 6,7-dihydro-1,4-dithiepin-2,3-dicarboxylic acid anhydride (15.1 g) in diphenyl ether at 200° C. in the presence of acetic acid (0.5 cc).

Preparation of 6-hydroxy-7-(5-nitropyrid-2-yl)-8-oxo-3,4,7,8-tetrahydro-2H,6H-dithiepino[1,4][2,3-c]-pyrrole (15.9 g), m.p. 200° C., by the action of sodium borohydride (1.7 g) on 6,8-dioxo-7-(5-nitropyrid-2-yl)-3,4,7,8-tetrahydro-2H,6H-dithiepino[1,4][2,3-c]pyrrole (19.4 g) in a mixture of tetrahydrofuran and methanol (5:1 by volume) at between −20° C. and +2° C.

EXAMPLE 7

Triethylamine (43 cc) is added, at 10° C., to a suspension of 7-(7-chloroquinol-2-yl)-6-hydroxy-8-oxo-3,4,7,8-tetrahydro-2H,6H-dithiepino[1,4][2,3-c]pyrrole (13.3 g) and of 1-chlorocarbonyl-4-methylpiperazine hydrochloride (44.0 g) in anhydrous methylene chloride (320 cc), and anhydrous pyridine (185 cc) is then added at 20° C. The reaction mixture is heated at 50° C. for 6 hours. After cooling, the mixture is diluted by adding methylene chloride (500 cc). The organic phase is washed seven times with distilled water (total 3.5 liters), dried over anhydrous magnesium sulphate and evaporated. The residue is dissolved in boiling ethanol (180 cc). After cooling for one hour at 2° C., the insoluble crystals are filtered off, washed twice with ethanol (total 20 cc), and twice with diethyl ether (total 20 cc) and dried under reduced pressure (20 mm Hg). The product obtained (13.6 g; m.p. 223° C.) is dissolved in dimethylformamide (245 cc) at 100° C. After filtering the hot solution, adding boiling acetonitrile (100 cc) to the filtrate and then cooling the mixture for 18 hours at 2° C., the resulting crystals are filtered off, washed twice with acetonitrile (total 100 cc) and dried under reduced pressure (0.2 mm Hg). 7-(7-Chloroquinol-2-yl)-6-(4-methylpiperazin-1-yl)-carbonyloxy-8-oxo-3,4,7,8-tetrahydro-2H,6H-dithiepino[1,4][2,3-c]pyrrole (11.9 g), melting at 223°–224° C., is thus obtained.

7-(7-Chloroquinol-2-yl)-6-hydroxy-8-oxo-3,4,7,8-tetrahydro-2H,6H-dithiepino[1,4][2,3-c]pyrrole used as starting material can be prepared in the following manner:

Preparation of 7-(7-chloroquinol-2-yl)-6,8-dioxo-3,4,7,8-tetrahydro-2H,6H-dithiepino[1,4][2,3-c]pyrrole (33.1 g), m.p. 250° C., by the action of 2-amino-7-chloroquinoline (17.9 g) on 6,7-dihydro-5H-1,4-dithiepin-2,3-dicarboxylic acid anhydride (20.2 g) in diphenyl ether at 150°–170° C. in the presence of anhydrous acetic acid (0.5 cc).

Preparation of 7-(7-chloroquinol-2-yl)-6-hydroxy-8-oxo-3,4,7,8-tetrahydro-2H,6H-dithiepino[1,4][2,3-c]pyrrole (9.1 g), m.p. 192° C., by the action of sodium borohydride (1.9 g) on 7-(7-chloroquinol-2-yl)-6,8-dioxo-3,4,7,8-tetrahydro-2H,6H-dithiepino[1,4][2,3-c]pyrrole (18.2 g) in a mixture of methanol and tetrahydrofuran (1:5 by volume) at between −20° C. and +2° C.

EXAMPLE 8

Triethylamine (18.2 cc) and anhydrous pyridine (65 cc) are added successively, at 10° C., to a suspension of 6-hydroxy-7-(1,8-naphthyridin-2-yl)-8-oxo-3,4,7,8-tetrahydro-2H,6H-dithiepino[1,4][2,3-c]pyrrole (3.9 g) and of 1-chlorocarbonyl-4-methylpiperazine hydrochloride (21.0 g) in anhydrous methylene chloride (150 cc). The reaction mixture is heated at 50° C. for 7 hours. After cooling, the mixture is diluted with methylene chloride (300 cc). The organic phase is washed three times with distilled water (total 360 cc), treated with decolourizing charcoal (1 g), dried over anhydrous magnesium sulphate and evaporated. The residue obtained (7.2 g) is treated with ethanol (80 cc). After cooling for 1 hour at 2° C., the insoluble crystals are filtered off, washed twice with iced ethanol (total 20 cc) and twice with diethyl ether (total 20 cc) and dried under reduced pressure (20 mm Hg). The product obtained in the form of the hydrochloride (4.4 g; m.p. 235°–240° C.) is dissolved in dimethylformamide (40 cc) at about 110° C. After cooling for 1 hour at 2° C., the resulting crystals are filtered off, washed with iced dimethylformamide (5 cc) and twice with diethyl ether (total 10 cc) and dried under reduced pressure (0.2 mm Hg). 6-(4-Methylpiperazin-1-yl)-carbonyloxy-7-(1,8-naphthyridin-2-yl)-8-oxo-3,4,7,8-tetrahydro-2H,6H-dithiepino[1,4][2,3-c]pyrrole hydrochloride (2.6 g), melting at 255° C. with decomposition, is thus obtained.

6-Hydroxy-7-(1,8-naphthyridin-2-yl)-8-oxo-3,4,7,8-tetrahydro-2H,6H-dithiepino[1,4][2,3-c]pyrrole used as starting material can be prepared in the following manner:

Preparation of 6,8-dioxo-7-(1,8-naphthyridin-2-yl)-3,4,7,8-tetrahydro-2H,6H-dithiepino[1,4][2,3-c]pyrrole (9.1 g), m.p. 252° C., by the action of 2-amino-1,8-naphthyridine (6.0 g) and 3-(3-diethylaminopropyl)-1-isopropyl-carbodiimide (8.1 g) on 6,7-dihydro-5H-1,4-dithiepin-2,3-dicarboxylic acid anhydride (8.35 g) in acetonitrile at the reflux temperature.

Preparation of 6-hydroxy-7-(1,8-naphthyridin-2-yl)-8-oxo-3,4,7,8-tetrahydro-2H,6H-dithiepino[1,4][2,3-c]pyrrole (3.9 g), m.p. 224° C., by the action of sodium borohydride (0.65 g) on 6,8-dioxo-7-(1,8-naphthyridin-2-yl)-3,4,7,8-tetrahydro-2H,6H-dithiepino[1,4][2,3- c]pyrrole (7.1 g) in a mixture of methanol and tetrahydrofuran (1:5 by volume) at between −20° C. and +2° C.

EXAMPLE 9

Triethylamine (70 cc) and anhydrous pyridine (270 cc) are added successively, at 10° C., to a suspension of 6-hydroxy-7-(7-methyl-1,8-naphthyridin-2-yl)-8-oxo-3,4,7,8-tetrahydro-2H,6H-dithiepino[1,4][2,3-c]pyrrole (15.6 g) and 1-chlorocarbonyl-4-methylpiperazine hydrochloride (80.0 g) in anhydrous methylene chloride (450 cc). The reaction mixture is heated at 50° C. for 7 hours. After cooling, the mixture is diluted with methylene chloride (500 cc). The organic phase is washed with 2N sodium hydroxide solution (500 cc) and six times with distilled water (total 3 liters), treated with decolourizing charcoal (2 g), dried over anhydrous magnesium sulphate and evaporated. The residue is dissolved in boiling ethanol (350 cc). After cooling for 18 hours at 2° C., the resulting crystals are filtered off, washed seven times with diisopropyl ether (total 350 cc) and dried under reduced pressure (20 mm Hg). The product obtained (6.9 g; m.p. 215° C.) is dissolved in a mixture of isopropanol (170 cc) and boiling ethanol (130 cc). After cooling for 18 hours at 2° C., the crystals which have appeared are filtered off, washed three times with diisopropyl ether (total 120 cc) and dried under reduced pressure (0.2 mm Hg). 7-(7-Methyl-1,8-naphthyridin-2-yl)-6-(4-methylpiperazin-1-yl)carbonyloxy-8-oxo-3,4,7,8-tetrahydro-2H,6H-dithiepino[1,4][2,3-c]pyrrole (3.4 g), melting at 230° C., is thus obtained.

6-Hydroxy-7-(7-methyl-1,8-naphthyridin-2-yl)-8-oxo-3,4,7,8-tetrahydro-2H,6H-dithiepino[1,4][2,3-c]pyrrole used as starting material can be prepared in the following manner:

Preparation of 6,8-dioxo-7-(7-methyl-1,8-naphthyridin-2-yl)-3,4,7,8-tetrahydro-2H,6H-dithiepino-[1,4][2,3-c]pyrrole (28.0 g), m.p. 256° C., by the action of 2-amino-7-methyl-1,8-naphthyridine (15.9 g) and 3-(3-diethylaminopropyl)-1-isopropyl-carbodiimide (19.8 g) on 6,7-dihydro-5H-1,4-dithiepin-2,3-dicarboxylic acid anhydride (20.2 g) in acetonitrile at the reflux temperature.

Preparation of 6-hydroxy-7-(7-methyl-1,8-naphthyridin-2-yl)-8-oxo-3,4,7,8-tetrahydro-2H,6H-dithiepino[1,4][2,3-c]pyrrole (7.7 g), m.p. 260° C., by the action of sodium borohydride (0.90 g) on 6,8-dioxo-7-(7-methyl-1,8-naphthyridin-2-yl)-3,4,7,8-tetrahydro-2H,6H-dithiepino[1,4][2,3-c]pyrrole (10.2 g) in a mixture of methanol and tetrahydrofuran (1:5 by volume) at between −20° C. and +2° C.

EXAMPLE 10

Triethylamine (8.1 cc) and anhydrous pyridine (34 cc) are added successively to a suspension of 6-hydroxy-7-(7-methoxy-1,8-naphthyridin-2-yl)-8-oxo-3,4,7,8-tetrahydro-2H,6H-dithiepino[1,4][2,3-c]pyrrole (1.9 g) and 1-chlorocarbonyl-4-methylpiperazine hydrochloride (9.4 g) in anhydrous methylene chloride (80 cc). The reaction mixture is heated at 50° C. for 9 hours. After cooling, the reaction mixture is treated with methylene chloride (180 cc) and N sodium hydroxide solution (80 cc). The organic phase is washed three times with distilled water (total 150 cc), dried over anhydrous magnesium sulphate and evaporated. The residue (4.7 g) is dissolved in boiling ethanol (40 cc). After cooling for 2 hours at 2° C., the resulting crystals are filtered off, washed with iced ethanol (8 cc) and diethyl ether (10 cc), and dried under reduced pressure (20 mm Hg). The product obtained (1.9 g; m.p. 204°–206° C.) is dissolved in boiling ethanol (34 cc). After cooling for 2 hours at 2° C., the crystals which have appeared are filtered off, washed twice with iced ethanol (total 10 cc) and with diethyl ether (10 cc) and dried under reduced pressure (0.2 mm Hg). 7-(7-Methoxy-1,8-naphthyridin-2-yl)-6-(4-methylpiperazin-1-yl)carbonyloxy-8-oxo-3,4,7,8-tetrahydro-2H,6H-dithiepino[1,4][2,3-c]-pyrrole (1.6 g), melting at 215° C., is thus produced.

6-Hydroxy-7-(7-methoxy-1,8-naphthyridin-2-yl)-8-oxo-3,4,7,8-tetrahydro-2H,6H-dithiepino[1,4][2,3-c]-pyrrole used as starting material can be prepared in the following manner:

Preparation of 6,8-dioxo-7-(7-methoxy-1,8-naphthyridin-2-yl)-3,4,7,8-tetrahydro-2H,6H-dithiepino-[1,4][2,3-c]pyrrole (11.1 g), m.p. 248° C., by the action of 2-amino-7-methoxy-1,8-naphthyridine (8.0 g) and of 3-(3-diethylaminopropyl)-1-isopropyl-carbodiimide (9.0 g) on 6,7-dihydro-5H-1,4-dithiepin-2,3-dicarboxylic acid anhydride (9.2 g) in acetonitrile at the reflux temperature.

Preparation of 6-hydroxy-7-(7-methoxy-1,8-naphthyridin-2-yl)-8-oxo-3,4,7,8-tetrahydro-2H,6H-dithiepino[1,4][2,3-c]pyrrole (1.0 g), m.p. 142° C., by the action of sodium borohydride (0.12 g) on 6,8-dioxo-7-(7-methoxy-1,8-naphthyridin-2-yl)-3,4,7,8-tetrahydro-2H,6H-dithiepino[1,4][2,3-c]pyrrole (1.5 g) in a mixture of methanol and tetrahydrofuran (1:5 by volume) at between −20° C. and +2° C.

EXAMPLE 11

Triethylamine (10.1 cc) is added, at 10° C., to a suspension of 7-(7-chloro-1,8-naphthyridin-2-yl)-6-hydroxy-8-oxo-3,4,7,8-tetrahydro-2H,6H-dithiepino[1,4][2,3-c]pyrrole (3.2 g) and 1-chlorocarbonyl-4-methylpiperazine hydrochloride (10.6 g) in anhydrous methylene chloride (50 cc), and anhydrous pyridine (50 cc) is then added at 20° C. The reaction mixture is heated at 50° C. for 6 hours. After cooling, the mixture is diluted by adding methylene chloride (250 cc). The organic phase is washed six times with distilled water (total 1.5 liters), dried over anhydrous magnesium sulphate and evaporated. The solid obtained is washed with ethanol (100 cc) and dried under reduced pressure (20 mm Hg). The product obtained (1.9 g; m.p. 280° C.) is dissolved in dimethylformamide (85 cc) at 100° C. After filtering the hot solution, adding boiling acetonitrole (140 cc) to the filtrate and then cooling the mixture for three hours at 2° C., the resulting crystals are filtered off, washed three times with acetonitrile (total 45 cc) and dried under reduced pressure (0.2 mm Hg). 7-(7-Chloro-1,8-naphthyridin-2-yl)-6-(4-methylpiperazin-1-yl)carbonyloxy-8-oxo-3,4,7,8-tetrahydro-2H,6H-dithiepino[1,4][2,3-c]pyrrole (1.5 g), melting at 283° C., is thus obtained.

7-(7-Chloro-1,8-naphthyridin-2-yl)-6-hydroxy-8-oxo-3,4,7,8-tetrahydro-2H,6H-dithiepino[1,4][2,3-c]pyrrole used as starting material can be prepared in the following manner:

Preparation of 7-(7-chloro-1,8-naphthyridin-2-yl)-6,8-dioxo-3,4,7,8-tetrahydro-2H,6H-dithiepino[1,4][2,3-c]pyrrole (11.2 g), m.p. 288° C., by the action of 2-amino-7-chloro-1,8-naphthyridine (8.4 g) and of 3-(3-diethylaminopropyl)-1-isopropyl-carbodiimide (9.25 g) on 6,7-dihydro-5H-1,4-dithiepin-2,3-dicarboxylic acid anhydride (9.45 g) in acetonitrile at the reflux temperature.

Preparation of 7-(7-chloro-1,8-naphthyridin-2-yl)-6-hydroxy-8-oxo-3,4,7,8-tetrahydro-2H,6H-dithiepino-[1,4][2,3-c]pyrrole (1.8 g), m.p. 242° C., by the action of sodium borohydride (0.33 g) on 7-(7-chloro-1,8-naphthyridin-2-yl)-6,8-dioxo-3,4,7,8-tetrahydro-2H,6H-dithiepino[1,4][2,3-c]pyrrole (4.6 g) in a mixture of methanol and tetrahydrofuran (1:5 by volume) at between −20° C. and +2° C.

EXAMPLE 12

Following the procedure of Example 11 but starting with 7-(7-chloro-1,8-naphthyridin-2-yl)-6-hydroxy-8-oxo-3,4,7,8-tetrahydro-2H,6H-dithiepino[1,4][2,3-c]pyrrole (7.3 g) and 1-chlorocarbonyl-4-ethylpiperazine hydrochloride (38.4 g) in a mixture of anhydrous methylene chloride (250 cc) and anhydrous pyridine (80 cc) in the presence of triethylamine (32 cc), 7-(7-chloro-1,8-naphthyridin-2-yl)-6-(4-ethylpiperazin-1-yl)carbonyloxy-8-oxo-3,4,7,8-tetrahydro-2H,6H-dithiepino-[1,4][2,3-c]pyrrole (7.4 g), melting at 254° C., is obtained after recrystallisation from acetonitrile (210 cc).

EXAMPLE 13

Following the procedure of Example 11 but starting with 7-(7-chloro-1,8-naphthyridin-2-yl)-6-hydroxy-8-oxo-3,4,7,8-tetrahydro-2H,6H-dithiepino[1,4][2,3-c]pyrrole (9.1 g) and 1-chlorocarbonyl-4-propylpiperazine hydrochloride (52.0 g) in a mixture of anhydrous methylene chloride (250 cc) and anhydrous pyridine (100 cc) in the presence of triethylamine (40 cc), 7-(7-chloro-1,8-naphthyridin-2-yl)-8-oxo-6-(4-propylpiperazin-1-yl)carbonyloxy-3,4,7,8-tetrahydro-2H,6H-dithiepino[1,4][2,3-c]pyrrole (7.9 g), melting at 225° C., is obtained after recrystallisation from acetonitrile (210 cc).

1-Chlorocarbonyl-4-propylpiperazine hydrochloride can be prepared from 1-propylpiperazine (64.0 g) and phosgene (99.0 g) in diethyl ether (550 cc) at 0° C. 1-Chlorocarbonyl-4-propylpiperazine hydrochloride (102.2 g), decomposing at about 270° C., is thus obtained.

EXAMPLE 14

Following the procedure of Example 11 but starting with 7-(7-chloro-1,8-naphthyridin-2-yl)-6-hydroxy-8-oxo-3,4,7,8-tetrahydro-2H,6H-dithiepino[1,4][2,3-c]pyrrole (7.3 g) and 1-chlorocarbonyl-4-isopropylpiperazine hydrochloride (41.6 g) in a mixture of anhydrous methylene chloride (250 cc) and anhydrous pyridine (80 cc) in the presence of triethylamine (32 cc), 7-(7-chloro-1,8-naphthyridin-2-yl)-6-(4-isopropylpiperazin-1-yl)carbonyloxy-8-oxo-3,4,7,8-tetrahydro-2H,6H-dithiepino[1,4][2,3-c]pyrrole (3.8 g), melting at 248° C., is obtained after recrystallisation from a mixture of dimethylformamide (15 cc) and acetonitrile (120 cc).

1-Chlorocarbonyl-4-isopropylpiperazine hydrochloride can be prepared from 1-isopropylpiperazine (64.0 g) and phosgene (99.0 g) in diethyl ether (400 cc) at 0° C. 1-Chlorocarbonyl-4-isopropylpiperazine hydrochloride (91.4 g), decomposing at about 270° C., is thus obtained.

EXAMPLE 15

Following the procedure of Example 11 but starting with 7-(7-chloro-1,8-naphthyridin-2-yl)-6-hydroxy-8-oxo-3,4,7,8-tetrahydro-2H,6H-dithiepino[1,4][2,3-c]pyrrole (11.0 g) and 4-allyl-1-chlorocarbonylpiperazine hydrochloride (61.8 g) in a mixture of anhydrous methylene chloride (300 cc) and anhydrous pyridine (120 cc) in the presence of triethylamine (48 cc), 6-(4-allylpiperazin-1-yl)carbonyloxy-7-(7-chloro-1,8-naphthyridin-2-yl)-8-oxo-3,4,7,8-tetrahydro-2H,6H-dithiepino[1,4][2,3-c]pyrrole (9.1 g), melting at 226° C., is obtained after recrystallisation from acetonitrile (440 cc).

EXAMPLE 16

Butanoic acid (0.90 cc) is added, at 20° C., to a suspension of 7-(7-chloro-1,8-naphthyridin-2-yl)-8-oxo-6-(piperazin-1-yl)carbonyloxy-3,4,7,8-tetrahydro-2H,6H-dithiepino[1,4][2,3-c]pyrrole (3.0 g) and dicyclohexylcarbodiimide (2.0 g) in anhydrous methylene chloride (60 cc). The reaction mixture is stirred at 20° C. for 2 hours. The dicyclohexylurea formed is removed in the first instance by filtering the reaction mixture (1.55 g) and secondly by extracting the residue, obtained after evaporation of the methylene chloride, with boiling ethanol (50 cc). The product obtained (3.1 g; m.p. 203° C. and then 230° C.) is dissolved in boiling acetonitrile (230 cc). After filtering the boiling solution, adding ethanol (20 cc) and cooling at 2° C. for 2 hours, the resulting crystals are filtered off, washed twice with iced acetonitrile (total 20 cc) and dried under reduced pressure (0.2 mm Hg). 6-(4-Butyrylpiperazin-1-yl)carbonyloxy-7-(7-chloro-1,8-naphthyridin-2-yl)-8-oxo-3,4,7,8-tetrahydro-2H,6H-dithiepino[1,4][2,3-c]pyrrole (2.6 g), melting at 210° C. and then at 230° C., is thus obtained.

7-(7-Chloro-1,8-naphthyridin-2-yl)-8-oxo-6-(piperazin-1-yl)carbonyloxy-3,4,7,8-tetrahydro-2H,6H-dithiepino[1,4][2,3-c]pyrrole used as starting material is prepared by the action of anhydrous trifluoroacetic acid (50 cc), at −10° C., on 6-(4-t-butoxycarbonylpiperazin-1-yl)carbonyloxy-7-(7-chloro-1,8-naphthyridin-2-yl)-8-oxo-3,4,7,8-tetrahydro-2H,6H-dithiepino[1,4][2,3-c]pyrrole (11.7 g). 7-(7-Chloro-1,8-naphthyridin-2-yl)-8-oxo-6-(piperazin-1-yl)carbonyloxy-3,4,7,8-tetrahydro-2H,6-dithiepino[1,4][2,3-c]pyrrole (4.8 g), melting at 295° C., is thus obtained.

6-(4-t-Butoxycarbonylpiperazin-1-yl)carbonyloxy-7-(7-chloro-1,8-naphthyridin-2-yl)-8-oxo-3,4,7,8-tetrahydro-2H,6H-dithiepino[1,4][2,3-c]pyrrole can be prepared in the following manner:

Triethylamine (3.5 cc) and anhydrous pyridine (50 cc) are added successively to a suspension of 7-(7-chloro-1,8-naphthyridin-2-yl)-6-hydroxy-8-oxo-3,4,7,8-tetrahydro-2H,6H-dithiepino[1,4][2,3-c]pyrrole (9.1 g) in methylene chloride (50 cc), and a solution of 4-chlorocarbonyl-1-t.-butoxycarbonylpiperazine (12.4 g) in methylene chloride (50 cc) is then added at 10° C. The reaction mixture is stirred at 20° C. for 2 hours and then diluted with methylene chloride (150 cc). The organic solution is washed twice with distilled water (total 250 cc), dried over anhydrous magnesium sulphate and evaporated. After recrystallising the residue obtained from a mixture of ethanol (250 cc) and dimethylformamide (60 cc), 6-(4-t-butoxycarbonylpiperazin-1-yl)carbonyloxy-7-(7-chloro-1,8-naphthyridin-2-yl)-8-oxo-3,4,7,8-tetrahydro-2H,6H-dithiepino[1,4][2,3-c]pyrrole (6.1 g), melting at 221° C., is obtained.

4-Chlorocarbonyl-1-t.-butoxycarbonylpiperazine can be prepared in the following manner:

Preparation of 1-t.-butoxycarbonylpiperazine (91.0 g), m.p. 60° C., by the action of t-butoxycarbonylazide (259.0 g) on piperazine monohydrochloride (310.0 g) in a mixture of water and dioxan (1:2 by volume) at 45° C.

Preparation of 4-chlorocarbonyl-1-t.-butoxycarbonylpiperazine (24.8 g), m.p. 99° C., by the action of phosgene (11.0 g) on 1-t.-butoxycarbonylpiperazine (40.8 g) in toluene at −5° C.

EXAMPLE 17

Following the procedure of Example 16 but starting with 7-(7-chloro-1,8-naphthyridin-2-yl)-8-oxo-6-(piperazin-1-yl)carbonyloxy-3,4,7,8-tetrahydro-2H,6H-dithiepino[1,4][2,3-c]pyrrole (7.1 g), dicyclohexylcarbodiimide (4.75 g) and propanoic acid (1.75 cc) in anhydrous methylene chloride (150 cc), 7-(7-chloro-1,8-naphthyridin-2-yl)-8-oxo-6-(4-propionylpiperazin-1-yl)carbonyloxy-3,4,7,8-tetrahydro-2H,6H-dithiepino[1,4][2,3-c]pyrrole (5.3 g), melting at 246° C., is obtained after recrystallisation from a mixture of acetonitrile (100 cc) and dimethylformamide (20 cc).

EXAMPLE 18

1-Methylpiperazine (1.1 g) is added to a suspension of 7-(5-chloropyrid-2-yl)-8-oxo-6-phenoxycarbonyloxy-3,4,7,8-tetrahydro-2H,6H-dithiepino[1,4][2,3-c]pyrrole (1.6 g) in acetonitrile (20 cc). The suspension obtained is stirred for 20 hours at about 20° C. The acetonitrile is evaporated under reduced pressure (20 mm Hg). The crystalline residue (2.4 g; m.p. about 150° C.) is dissolved in methylene chloride (40 cc). The methylene chloride solution is washed with N sodium hydroxide solution (40 cc) and extracted twice with a 0.1N aqueous methanesulphonic acid solution (total 200 cc). The combined acid aqueous extracts are rendered alkaline by the addition of about 10N sodium hydroxide solution. The oil which separates out is extracted twice with methylene chloride (total 80 cc). The organic solution is washed twice with distilled water (total 100 cc), dried over anhydrous magnesium sulphate and evaporated. The product obtained (1.6 g; m.p. 153° C.) is dissolved in boiling acetonitrile (4 cc), and boiling ethanol (14 cc) is added. After cooling the solution at 2° C. for 2 hours, the resulting crystals are filtered off, washed with iced ethanol (5 cc) and dried under reduced pressure (0.2 mm Hg). 7-(5-Chloropyrid-2-yl)-6-(4-methylpiperazin-1-yl)carbonyloxy-8-oxo-3,4,7,8-tetrahydro-2H,6H-dithiepino[1,4][2,3-c]pyrrole (0.7 g), melting at 156° C., is thus obtained.

7-(5-Chloropyrid-2-yl)-8-oxo-6-phenoxycarbonyloxy-3,4,7,8-tetrahydro-2H,6H-dithiepino[1,4][2,3-c]pyrrole can be prepared by the action of phenyl chloroformate (3.14 g) on 7-(5-chloropyrid-2-yl)-6-hydroxy-8-oxo-3,4,7,8-tetrahydro-2H,6H-dithiepino[1,4][2,3-c]pyrrole (2.10 g) in anhydrous pyridine (25 cc) at a temperature between −10° C. and 20° C. After recrystallisation from acetonitrile (50 cc), 7-(5-chloropyrid-2-yl)-8-oxo-6-phenoxycarbonyloxy-3,4,7,8-tetrahydro-2H,6H-dithiepino[1,4][2,3-c]pyrrole (1.73 g), melting at 173° C., is obtained.

The present invention includes within its scope pharmaceutical compositions which comprise, as active ingredient, at least one of the compounds of general formula I, or — when appropriate — a non-toxic acid addition salt thereof, in association with a pharmaceutical carrier or coating. The invention includes especially such preparations made up for oral, parenteral, rectal or percutaneous administration.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water or liquid paraffin. Besides inert diluents such compositions may also comprise adjuvants, such as wetting, emulsifying and suspending agents, and sweetening, flavouring and aromatizing agents. The compositions according to the invention, for oral administration, also include capsules of absorbable material such as gelatin containing the active substance with or without the addition of diluents or excipients.

Preparations according to the invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilized by, for example, filtration through a bacteria-retaining filter, by incorporation in the compositions of sterilizing agents, by irradiation, or by heating. They may also be manufactured in the form of sterile solid compositions, which can be dissolved in sterile water or some other sterile injectable medium immediately before use.

Compositions for rectal administration are suppositories which contain, in addition to the active substance, excipients such as cacao butter or a suitable wax base.

The percentage of active ingredient in the compositions of the invention may be varied, it being necessary that is should constitute a proportion such that a suitable dosage shall be obtained. The dosage depends on the desired therapeutic effect, on the route of administration and on the duration of the treatment. The compositions are particularly useful in human therapy because of their tranquillising effects, their anti-convulsant effect, their effect in overcoming contractures and their effect in producing hypnosis. In human therapy the compositions when administered orally to an adult should generally give doses between 10 mg and 500 mg of active substance per day. In general the physician will decide the posology considered appropriate, taking into account the age and weight and other factors intrinsic to the patient being treated.

The following Example illustrates pharmaceutical compositions according to the invention

EXAMPLE 19

Tablets containing 25 mg of active product and having the following composition are prepared in accordance with the usual technique:

7-(7-chloro-1,8-naphthyridin-2-yl)-6-(4-methylpiperazin-1-yl)carbonyloxy-8-oxo-3,4,7,8-tetrahydro-2H,6H-dithiepino[1,4][2,3-c]pyrrole 0.025 g

| starch | 0.090 g |
|---|---|
| precipitated silica | 0.030 g |
| magnesium stearate | 0.005 g. |

We claim:

1. A dithiepino[1,4][2,3-c]pyrrole compound of the formula:

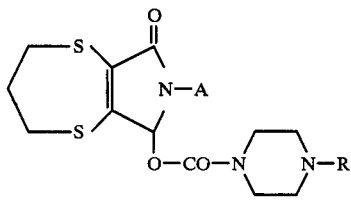

wherein A represents pyrid-2-yl or 1,8-naphthyridin-2-yl, or pyrid-2-yl or 1,8-naphthyridin-2-yl substituted by one halogen, alkyl of 1 through 4 carbon atoms, or alkoxy of 1 through 4 carbon atoms, and R represents alkyl of 1 through 4 carbon atoms or alkenyl of 2 through 4 carbon atoms, and non-toxic pharmaceutically acceptable acid addition salts thereof.

2. A dithiepino[1,4][2,3-c]pyrrole compound according to claim 1 wherein R represents alkyl of 1 through 4 carbon atoms or alkenyl of 3 or 4 carbon atoms.

3. A dithiepino[1,4][2,3-c]pyrrole compound according to claim 1 in which in A the halogen is chlorine, the alkoxy is methoxy, the alkyl is methyl, and, in R, the alkyl is methyl and the alkenyl is allyl.

4. The dithiepino[1,4][2,3-c]pyrrole compound according to claim 1 which is 7-(5-chloropyrid-2-yl)-6-(4-methylpiperazin-1-yl)carbonyloxy-8-oxo-3,4,7,8-tetrahydro-2H,6H-dithiepino[1,4][2,3-c]pyrrole and its non-toxic pharmaceutically acceptable acid addition salts.

5. The dithiepino[1,4][2,3-c]pyrrole compound according to claim 1 which is 7-(7-methoxy-1,8-naphthyridin-2-yl)-6-(4-methylpiperazin-1-yl)carbonyloxy-8-oxo-3,4,7,8-tetrahydro-2H,6H-dithiepino[1,4][2,3-c]pyrrole and its non-toxic pharmaceutically acceptable acid addition salts.

6. The dithiepino[1,4][2,3-c]pyrrole compound according to claim 1 which is 7-(7-chloro-1,8-naphthyridin-2-yl)-6-(4-methylpiperazin-1-yl)carbonyloxy-8-oxo-3,4,7,8-tetrahydro-2H,6H-dithiepino[1,4][2,3-c]pyrrole and its non-toxic pharmaceutically acceptable acid addition salts.

7. The dithiepino[1,4][2,3-c]pyrrole compound according to claim 1 which is 6-(4-allylpiperazin-1-yl)carbonyloxy-7-(7-chloro-1,8-naphthyridin-2-yl)-8-oxo-3,4,7,8-tetrahydro-2H,6H-dithiepino[1,4][2,3-c]pyrrole and its non-toxic pharmaceutically acceptable acid addition salts.

8. The dithiepino[1,4][2,3-c]pyrrole compound according to claim 1 which is 7-(5-chloropyrid-2-yl)-6-(4-ethylpiperazin-1-yl)carbonyloxy-8-oxo-3,4,7,8-tetrahydro-2H,6H-dithiepino[1,4][2,3-c]pyrrole and its non-toxic pharmaceutically acceptable acid addition salts.

9. The dithiepino[1,4][2,3-c]pyrrole compound according to claim 1 which is 6-(4-allylpiperazin-1-yl)-carbonyloxy-7-(5-chloropyrid-2-yl)-8-oxo-3,4,7,8-tetrahydro-2H,6-dithiepino[1,4][2,3-c]pyrrole and its non-toxic pharmaceutically acceptable acid addition salts.

10. The dithiepino[1,4][2,3-c]pyrrole compound according to claim 1 which is 6-(4-methylpiperazin-1-yl)-carbonyloxy-7-(1,8-naphthyridin-2-yl)-8-oxo-3,4,7,8-tetrahydro-2H,6H-dithiepino[1,4][2,3-c]pyrrole and its non-toxic pharmaceutically acceptable acid addition salts.

11. The dithiepino[1,4][2,3-c]pyrrole compound according to claim 1 which is 7-(7-chloro-1,8-naphthyridin-2-yl)-6-(4-ethylpiperazin-1-yl)carbonyloxy-8-oxo-3,4,7,8-tetrahydro-2H,6H-dithiepino[1,4][2,3-c]pyrrole and its non-toxic pharmaceutically acceptable acid addition salts.

12. The dithiepino[1,4][2,3-c]pyrrole compound according to claim 1 which is 7-(7-chloro-1,8-naphthyridin-2-yl)-8-oxo-6-(4-propylpiperazin-1-yl)carbonyloxy-3,4,7,8-tetrahydro-2H,6H-dithiepino[1,4][2,3-c]pyrrole and its non-toxic pharmaceutically acceptable acid addition salts.

13. The dithiepino[1,4][2,3-c]pyrrole compound according to claim 1 which is 7-(7-chloro-1,8-naphthyridin-2-yl)-6-(4-isopropylpiperazin-1-yl)carbonyloxy-8-oxo-3,4,7,8-tetrahydro-2H,6H-dithiepino[1,4][2,3-c]pyrrole and its non-toxic pharmaceutically acceptable acid addition salts.

14. The dithiepino[1,4][2,3-c]pyrrole compound according to claim 1 which is 6-(4-methylpiperazin-1-yl)carbonyloxy-7-(5-methylpyrid-2-yl)-8-oxo-3,4,7,8-tetrahydro-2H,6H-dithiepino[1,4][2,3-c]pyrrole and its non-toxic pharmaceutically acceptable acid addition salts.

15. A pharmaceutical composition useful as a tranquilliser, anti-convulsant agent, decontracturant and agent to produce hypnosis which comprises an effective amount of a dithiepino[1,4][2,3-c]pyrrole compound as claimed in claim 1, or a non-toxic pharmaceutically acceptable acid addition salt thereof, in association with a pharmaceutical carrier.

* * * * *